United States Patent [19]
Klardie et al.

[11] Patent Number: 6,048,204
[45] Date of Patent: Apr. 11, 2000

[54] SELF TAPPING SCREW TYPE DENTAL IMPLANT

[75] Inventors: Michael R. Klardie, Bloomington; Jeremy M. Huotari, Mound; Thomas A. Tremmel, Minneapolis, all of Minn.

[73] Assignee: Lifecore Biomedical, Inc., Chaska, Minn.

[21] Appl. No.: 09/218,378

[22] Filed: Dec. 22, 1998

Related U.S. Application Data

[63] Continuation-in-part of application No. 09/018,030, Feb. 3, 1998.

[51] Int. Cl.$^7$ ..................................................... A61C 8/00
[52] U.S. Cl. ............................................................ 433/174
[58] Field of Search ................................... 433/172, 173, 433/174

[56] References Cited

U.S. PATENT DOCUMENTS

| | | |
|---|---|---|
| Re. 35,784 | 5/1998 | Linkow et al. ................... 433/174 |
| D. 296,362 | 6/1988 | Branemark . |
| 2,609,604 | 9/1952 | Sprague . |
| 3,732,621 | 5/1973 | Bostrom . |
| 3,905,109 | 9/1975 | Cohen et al. . |
| 4,229,169 | 10/1980 | Smith et al. . |
| 4,406,623 | 9/1983 | Grafelmann et al. . |
| 4,407,620 | 10/1983 | Shinjo . |
| 4,416,629 | 11/1983 | Mozsary et al. . |
| 4,468,200 | 8/1984 | Münch . |
| 4,712,681 | 12/1987 | Bránemark et al. . |
| 4,713,004 | 12/1987 | Linkow et al. . |
| 4,730,969 | 3/1988 | Dohi . |
| 4,781,506 | 11/1988 | Roberts et al. . |
| 4,842,518 | 6/1989 | Linkow et al. . |
| 4,932,868 | 6/1990 | Linkow et al. . |
| 5,064,425 | 11/1991 | Branemark et al. ............ 433/174 X |
| 5,269,685 | 12/1993 | Jörnéus et al. ..................... 433/174 |
| 5,316,520 | 5/1994 | Green . |
| 5,338,197 | 8/1994 | Kwan ............................... 433/174 |
| 5,427,527 | 6/1995 | Niznick et al. . |
| 5,571,017 | 11/1996 | Niznick . |
| 5,642,996 | 7/1997 | Mochida et al. ................ 433/174 |
| 5,704,750 | 1/1998 | Bartos et al. . |
| 5,727,943 | 3/1998 | Beaty et al. ..................... 433/174 |
| 5,772,437 | 6/1998 | Rangert et al. ................. 433/174 |
| 5,816,812 | 10/1998 | Kownacki et al. . |
| 5,842,865 | 2/1999 | Bassett et al. .................. 433/174 |
| 5,897,319 | 4/1999 | Wagner et al. .................. 433/174 |
| 5,902,109 | 5/1999 | Reams, III et al. ............. 433/174 |

FOREIGN PATENT DOCUMENTS

| | | |
|---|---|---|
| 0 111 134 A1 | 6/1984 | European Pat. Off. . |
| 0 126 624 A2 | 11/1984 | European Pat. Off. . |
| 0 139 052 A1 | 5/1985 | European Pat. Off. . |
| 0237505 | 9/1987 | European Pat. Off. .......... A61C 8/00 |
| 0 263 274 B1 | 4/1988 | European Pat. Off. . |
| 0 288 702 A2 | 11/1988 | European Pat. Off. . |
| 0 323 559 A2 | 7/1989 | European Pat. Off. . |
| 0 323 559 A3 | 7/1989 | European Pat. Off. . |
| 0 449 334 B1 | 10/1991 | European Pat. Off. . |
| 0 458 258 A | 11/1991 | European Pat. Off. . |
| 0 530 160 A1 | 3/1993 | European Pat. Off. . |
| 2 667 499 A1 | 4/1992 | France . |
| 3043336 C2 | 6/1981 | Germany . |
| 3626172 A1 | 2/1988 | Germany . |
| 95/17135 | 6/1995 | WIPO . |

OTHER PUBLICATIONS

"Cutting Tool Design," *Fundamentals of Tool Design*, 2:124–127 (1984).

"Taps and Threading Dies," pp. 1686–1689 (date unknown).

"Self–Threading Screws," *Machinery's Handbook*, 24:1454–1457; 868–869; 844–847 (1992).

Core–Vent Corporation Product Brochure for SCREW–VENT™ (date unknown).

The VentPlant Corporation, Family of Compatible Implant Systems, pp. 1–12 (date unknown).

1988 Product Catalog, Brånemark System™, The Unique Method of Osseointegration for Restorative Dentistry.

Brånemark, et al., "Osseointegrated implants in the Treatment of the Edentulous Jaw," *Suppl. to Scandinavian Journal of Plastic and Reconstructive Surgery*, pp. 30–33 (1977).

Ledermann, et al., "The Ha–Ti Implant," *Schweiz Monatsschr Zahnmed*, 101:611–615 (1991).

"Bone Screw Technical Information," ©Richard Manfacturing Co. Inc. pp. 1–14 (1980).

Friberg, et al., "A New Self–Tapping Brånemark Implant: Clinical and Radiographic Evaluation," *The International Journal of Oral & Maxillofacial Implants*, 7:80–85 (1992).

Paragon Implant Company Product brochure for Complete Implant™ (date unknown).

3i Synergy, Surgical Choices with Restorative Simplicity (date unknown).

MIT Minimatic Implant Technology Product Catalog for Screw Implants, p. 5. (date unknown).

Introducing The MAESTRO™ System, Division A Implants (date unknown).

Sulzer Calcitek Inc. Product Brochure for Spline Dental Implant System (1996).

"IMTEC, Hexed–Head™ Implant System," *Surgical and Prosthetic Catalog*, 5th Edition (date unknown).

Swede–Vent™, Product Catalog, The external hex system from Dentsply (1992).

Adell, et al., "A 15–year study of Osseointegrated implants in the treatment of the edentulous jaw," *Int. J. Oral Surg*, 10:387–416 (1981).

Laney, et al., "Dental Implants: Tissue–Integrated Prosthesis Utilizing the Osseointegration Concept," Mayo Clinic Proceedings, 61:91–97 (Feb. 1986).

The Unique Method of Tissue Integration That Offers Patients New Quality Life (1985).

"IMZ® TwinPlus," *Implant Prosthetics* (date unknown).

3i Implant Innovations Product Brochure, ICE, Incremental Cutting Edges Super Self–Tapping Implant, 1996.

Branemark System Product Catalog (Nobelpharma) 1989–1990.

Sulzer Calcitek Inc. Product Brochure for Spline Twist™ Implants, Jul., 1997.

Implant Support Systems, Inc., Catalog Summer 1993.

*Primary Examiner*—Nicholas D. Lucchesi
*Attorney, Agent, or Firm*—Vidas, Arrett & Steinkraus

[57] ABSTRACT

A self-tapping screw-shaped dental implant for implantation in bone tissue is disclosed. The implant serves as an anchor for artificial teeth, tooth bridges or other dental prostheses and comprises a screw body with an external thread. The implant is characterized by one or more cavities in the screw body. The cavities include a cutting edge with cutting teeth. At least one of the cutting teeth is provided with a beveled relief surface defined on the outer surface of the implant behind the cutting tooth and at least one of the cutting teeth is provided with a full threaded outer surface on the implant behind the cutting tooth. In the case of multiple cavities, the cavities may extend to different heights along the screw body. The implant is also characterized in that the upper surface of the each of the cavities is parallel to the thread.

32 Claims, 7 Drawing Sheets

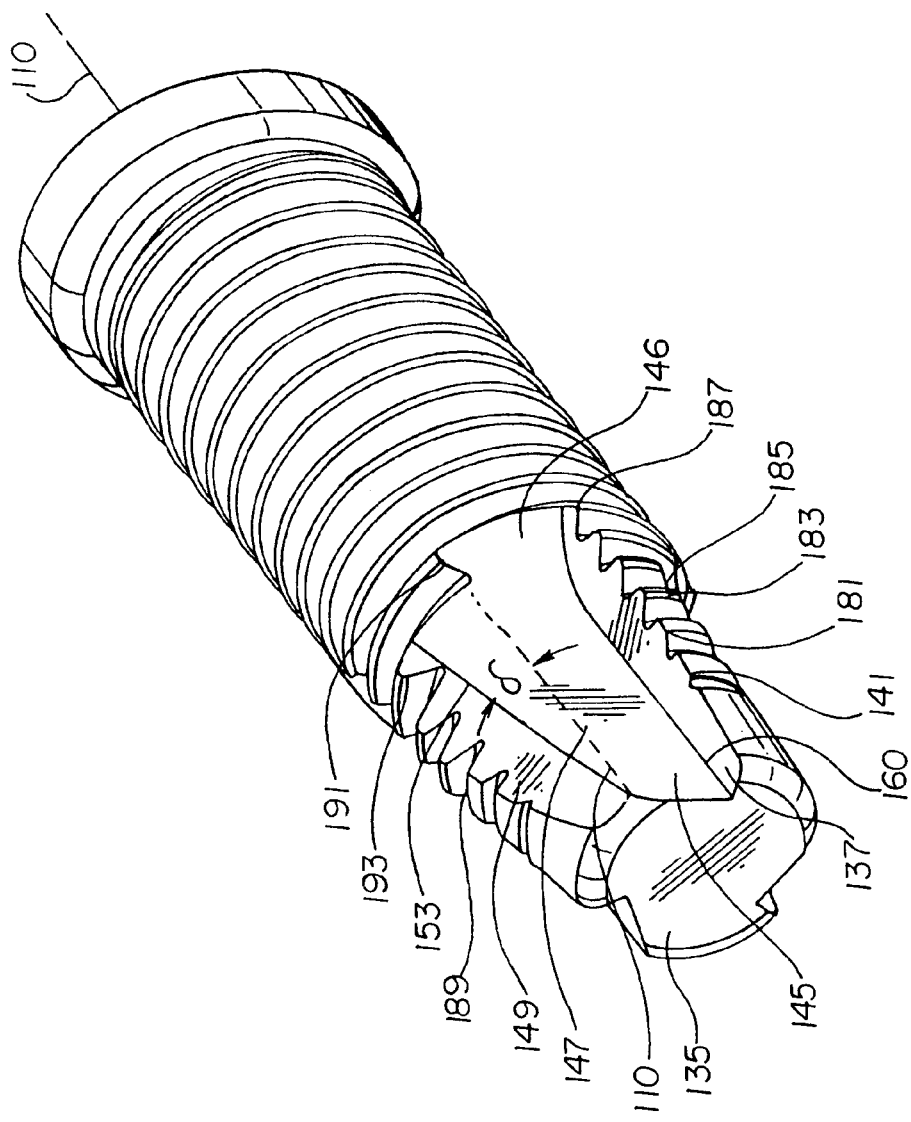

SELF TAPPING SCREW TYPE DENTAL IMPLANT

The present invention is a continuation-in-part of U.S. application Ser. No. 09/018030 filed Feb. 3, 1998, the contents of which are incorporated herein in their entirety by reference.

FIELD OF THE INVENTION

The present invention relates to a self tapping screw type dental implant which provides good tapping ability into cortical or trabecular bone. The tip of the implant comprises three cavities formed on the outer surface of the implant. The edges of the cavities form cutting edges to provide self-tapping when the implant is screwed into bone tissue. The cavities are designed to contain the bone tissue that is chipped off by the cutting edges.

BACKGROUND OF THE INVENTION

In order to surgically place a threaded dental implant, a pilot hole is drilled into the bone in which the implant will be placed. Successively larger diameter drill bits are then used to increase the hole to the minor diameter of the threaded implant. A screw tap is then used to form a thread pattern in the bone forming the walls of the bore.

To eliminate the need for a separate tapping step prior to implantation, self-tapping screw implants have been developed. EP 0 237 505 to Jörnéus discloses a screw shaped anchoring implant with cavities formed from two mutually perpendicular through holes which are also perpendicular to the longitudinal axis of the implant or by three cavities formed on the outer, circular surface of the implant so that the cutting edges have a positive cutting angle.

U.S. Pat. No. 5,269,685 to Jörnéus et al. describes a screw-shaped titanium anchoring member comprising at least one cavity located at the forward tip of the screw. The edges of the cavity form a cutting surface. A clearance is provided behind the cutting edges. The clearance is provided by slightly beveling the outer surface behind the cutting edge.

Restore™, a self-tapping screw implant manufactured by Lifecore Biomedical, Inc., has four chip cavities formed on the outer surface of the dental implant so that the cutting surfaces form a zero rake angle.

Other self-tapping screw implants are also commercially available.

In spite of the utility of self-tapping implants, it can be difficult, in particular in dense cortical bone, to seat self-tapping screw implants. Self-tapping implants for dense bone must have excellent cutting characteristics to avoid damaging the implant and/or the surrounding bone.

It is a goal of the present invention to provide a self-tapping screw type dental implant which will provide excellent tapping ability into dense bone such as Type 1 (D1), (Misch CE: Contemporary Implant Density, 1993).

SUMMARY OF THE INVENTION

The object of the present invention, providing a self tapping screw type dental implant has been achieved by providing an implant with one or more cutting edges, the cutting edges and other implant surfaces angled in such a way as to efficiently deposit cut bone material into cavities formed in the implant while allowing for efficient tapping.

The implant has an upper portion and a lower portion and is formed from a screw body with an external thread. At least one longitudinal cavity is formed within the lower portion. One of the surfaces of the cavity forms a cutting face with a cutting edge to provide self-tapping. The cutting edge has a plurality of cutting teeth including at least one cutting tooth provided with a beveled relief surface defined on the outer surface of the implant behind the cutting tooth and at least one cutting tooth with a full thread on the outer surface of the implant behind the cutting tooth.

In another embodiment, the invention is directed to a self tapping screw-shaped dental implant having a screw body with an external thread. The body has a top which includes an upper portion with an attachment means for attaching a dental prosthesis thereto, and a lower portion extending downward from the upper portion. The lower portion terminates in a base lying in a plane perpendicular to the longitudinal axis of the implant. The lower portion has at least one chip cavity therein. The at least one cavity is defined by at least two surfaces including a cutting face surface having a cutting edge with first cutting teeth and a second surface disposed at an angle relative to the cutting face surface. The second surface includes at least a plurality of second teeth including at least one beveled tooth and at least one tooth which is not beveled.

In another embodiment, the invention is directed to a dental implant consisting of a threaded body including an upper portion and a substantially frustoconical shaped lower portion. At least one opening is present in the lower portion. The lower portion also includes a threaded portion which includes at least one beveled portion which terminates in a cutting tooth at the opening and at least one non-beveled portion which terminates in a cutting tooth at the opening.

In another embodiment, the invention is directed to a dental implant whose lower portion has a plurality of circumferentially adjacent cavities therein. Each cavity has an uppermost part. The uppermost part of at least one cavity is disposed closer to the top than the uppermost part of at least one other cavity.

The invention is also directed to a dental implant with cavities therein, each cavity having an upper portion which is bounded by an edge, wherein the edge of each cavity lies along the thread and is substantially parallel to the thread. The edge may lie along the leading surface, the trailing surface or the crest of the thread.

BRIEF DESCRIPTION OF THE FIGURES

FIG. 7 is a perspective view of another embodiment of the invention.

DETAILED DESCRIPTION OF THE INVENTION

Figure 1:
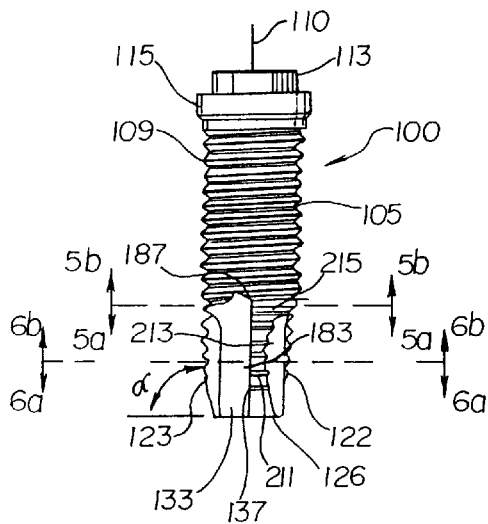
FIG. 1 is a side elevational view of the self tapping screw type dental implant according to the present invention.
Figure 2:
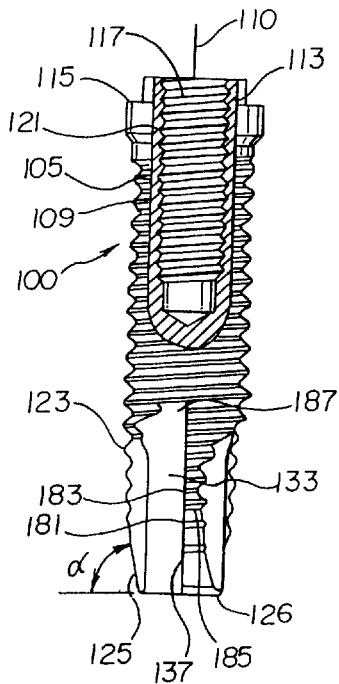
FIG. 2 is a side elevational view with parts cut away of the self tapping screw type dental implant according to the present invention.

As illustrated in FIG. 1, the self tapping screw type dental implant shown generally as 100, comprises a screw body 105 with an external thread 109. Implant 100 is characterized by a longitudinal axis 110. The implant is intended to be inserted in a bored hole in the jaw for permanent anchoring of artificial teeth, tooth-bridges and other dental implants. The upper end 113 of the implant has an optional collar 115 and an attachment means for attaching a dental prosthesis thereto. As depicted in FIG. 2, the attachment means is a bore 117 within upper end 113, the bore being threaded 121 to accept threaded inserts. Of course, the attachment means may be of any other suitable design for attaching a dental prosthesis such as a male part extending upwards from the upper portion. Optionally, the male part may be threaded.

The inventive self tapping screw type dental implant may be made of Ti-6A1-4V E.L.I. (ASTM F136) commercially pure titanium. (ASTM F67) grade 3, although other grades of commercially pure titanium such as grades 1, 2 and 4 of commercially pure titanium (ASTM F67) may also be used depending on the desired shape and strength characteristics of the implant. Other suitable biocompatible materials may be used as well.

Figure 3:
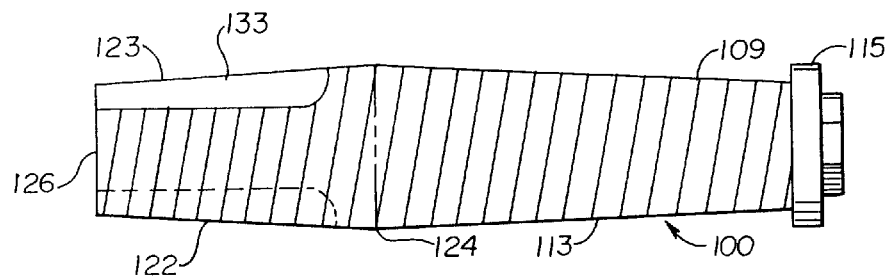
FIG. 3 is a schematic drawing of the dental implant according to the present invention.

The general shape of dental implant is seen in FIG. 3. Implant 100 has a substantially frustoconical shaped upper end 113 and a frustoconical shaped lower end 122. Thread 109 tapers inward from region 124 of maximum thread diameter toward base 126 of the implant. Thread 109 also tapers inward from a region 124 upward toward collar 115. For the sake of clarity, the tapering of the thread refers to a decrease in thread major and minor diameters along the length of the implant.

Desirably, the screw body itself is also generally tapered inward in the downward direction toward the base so that at least portion of the screw body is substantially frustoconical. The tapering of the screw body preferably starts from the region of maximum diameter of the screw body and extends to the base of the screw body. Also desirably, the screw body is tapered inward in the upward direction from the region of maximum screw body diameter to the top of the screw body. Preferably, the angle of the taper in one or both of the lower and upper portions of the screw body will match or be substantially similar to the angle of the taper of the external thread in the lower and/or upper portions of the implant.

The invention also contemplates the use of other shaped screw bodies such as substantially cylindrical screw bodies.

The lower end of the implant shown generally at 123, has a conical, chamfered implant tip 125 to facilitate the insertion of the implant into the bored hole in the bone tissue. Although FIG. 1 depicts an implant tip with an apical implant chamfer, denoted by α, at a desired angle of 80° relative to a plane perpendicular to the longitudinal axis of the implant, the apical implant chamfer may range from 15° to 85°.

The lower end of the implant 123 is provided with one or more cavities or openings 133 on the surface of the implant. Desirably, the implant will have a plurality of cavities. More desirably, three or four cavities will be present, symmetrically distributed about the screw body of the implant. The one or more cavities 133 are longitudinal and desirably, although not necessarily, extend downward to the base 126 of the implant.

Figure 4:
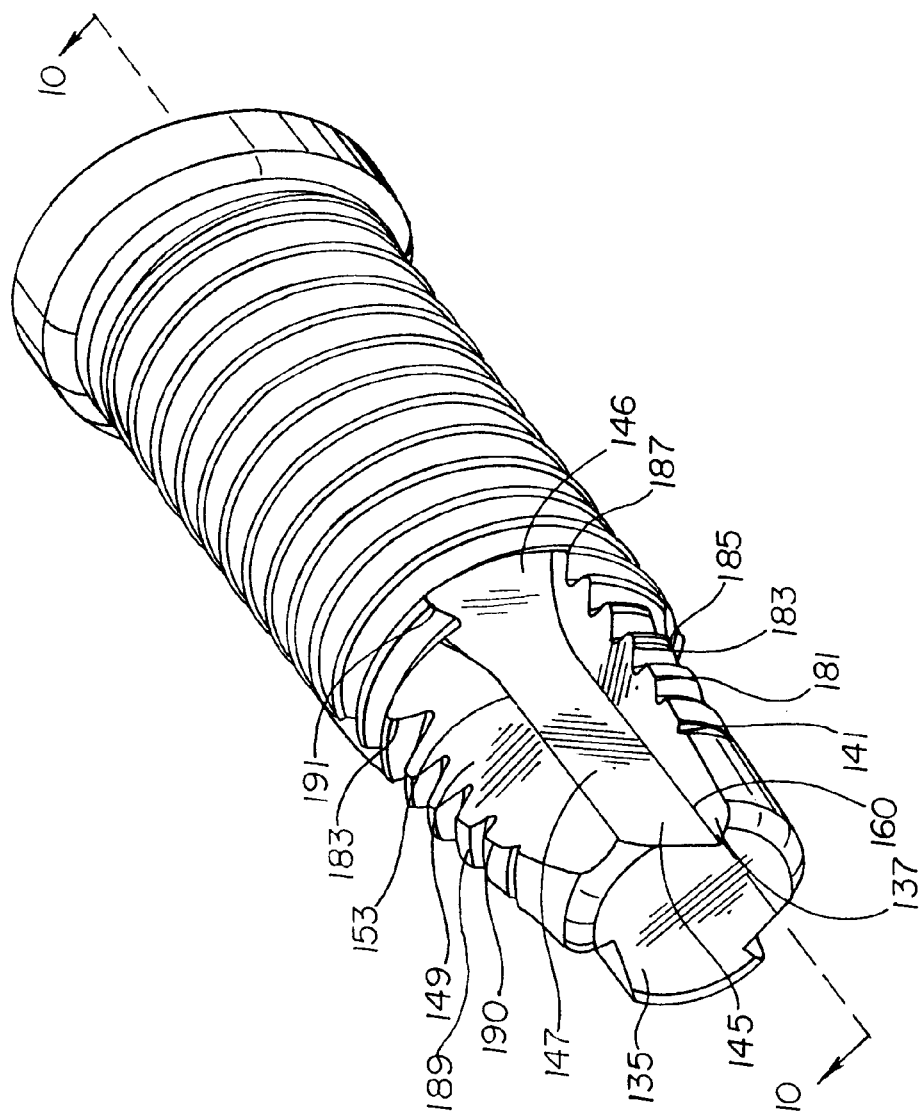
FIGS. 4 is a perspective view of the inventive implant shown in FIG. 1.

Each cavity is partially bounded by a plurality of surfaces as shown in FIG. 4. The first surface, designated the cutting face 137, is a straight, plane surface with a cutting edge 141. The second surface, designated the concave surface 145 is desirably flat in a region by the base 135 of the implant, designated by reference numeral 147, and concave in part, the concave part designated by reference numeral 146, as seen in FIG. 4. Cutting face 137 and flat part 147 of concave surface 145 are shown perpendicular to one another although they need not be perpendicular. Other cavity shapes may be used as well in conjunction with the inventive features disclosed herein.

Figure 5A:
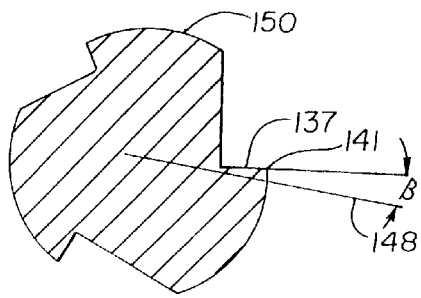
FIG. 5a is a downward looking transverse cross section along lines 5a—5a of FIG. 1.
Figure 6A:
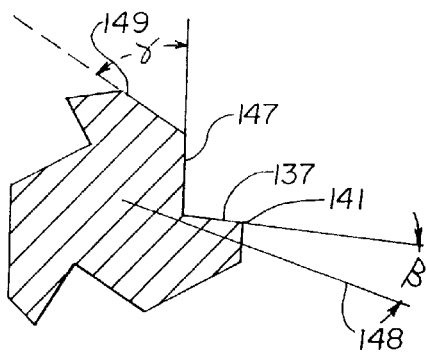
FIG. 6a is a downward looking transverse cross section along lines 6a—6a of FIG. 1.

The intersection between cutting face 137 and the flat part 147 of concave surface 145 defines a line, designated by reference numeral 160. As shown in FIGS. 5a and 6a, cutting face 137 is disposed at an angle β, designated the rake angle, relative to a radial plane 148 intersecting line 160. The rake angle β ranges from about 2° to about 15° degrees as depicted in FIG. 4. In a preferred embodiment, rake angle β ranges from 3° to about 5° while in a more preferred embodiment, rake angle β is 3°. The positive rake angle produces an increased shearing plane thus facilitating increased cutting performance. A third surface 149, designated the relief surface, forms a second acute angle, designated the flat relief angle and denoted by γ, with the flat region 147. Relief surface 149 is formed by beveling the thread behind cutting edge 141. Flat relief angle γ ranges from about 30° to about 70° and preferably, is about 60°.

FIGS. 5a, a downward looking cross section through a beveled portion of the implant and 6a, a downward looking cross section through a non-beveled portion of the implant, further highlight one of the many inventive features of the implant disclosed herein, namely, the presence of cutting teeth followed by a full threaded screw surface 150, as in FIG. 5a and cutting teeth followed by a beveled screw surface 149 as FIG. 6a.

Figure 5B:
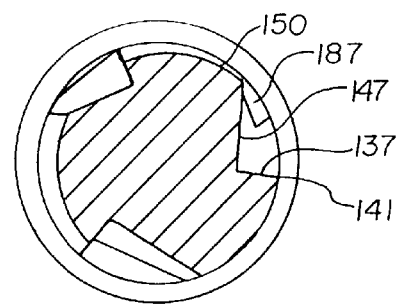
FIG. 5b is an upward looking transverse cross section along lines 5b—5b of FIG. 1.
Figure 6B:
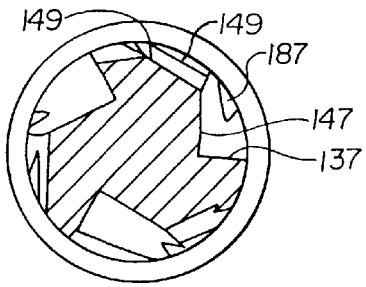
FIG. 6b is an upward looking transverse cross section along lines 6b—6b of FIG. 1.

FIGS. 5b and 6b, upward looking cross-sections through the beveled and non-beveled portions further contribute to an understanding of the invention. FIG. 5b shows fully threaded outer surface 150 behind the cutting tooth as well an additional cutting tooth 187 with a threaded outer surface further toward the top of the implant. FIG. 6b shows an upward succession of beveled threads, as well as non-beveled tooth 187.

Figure 8:
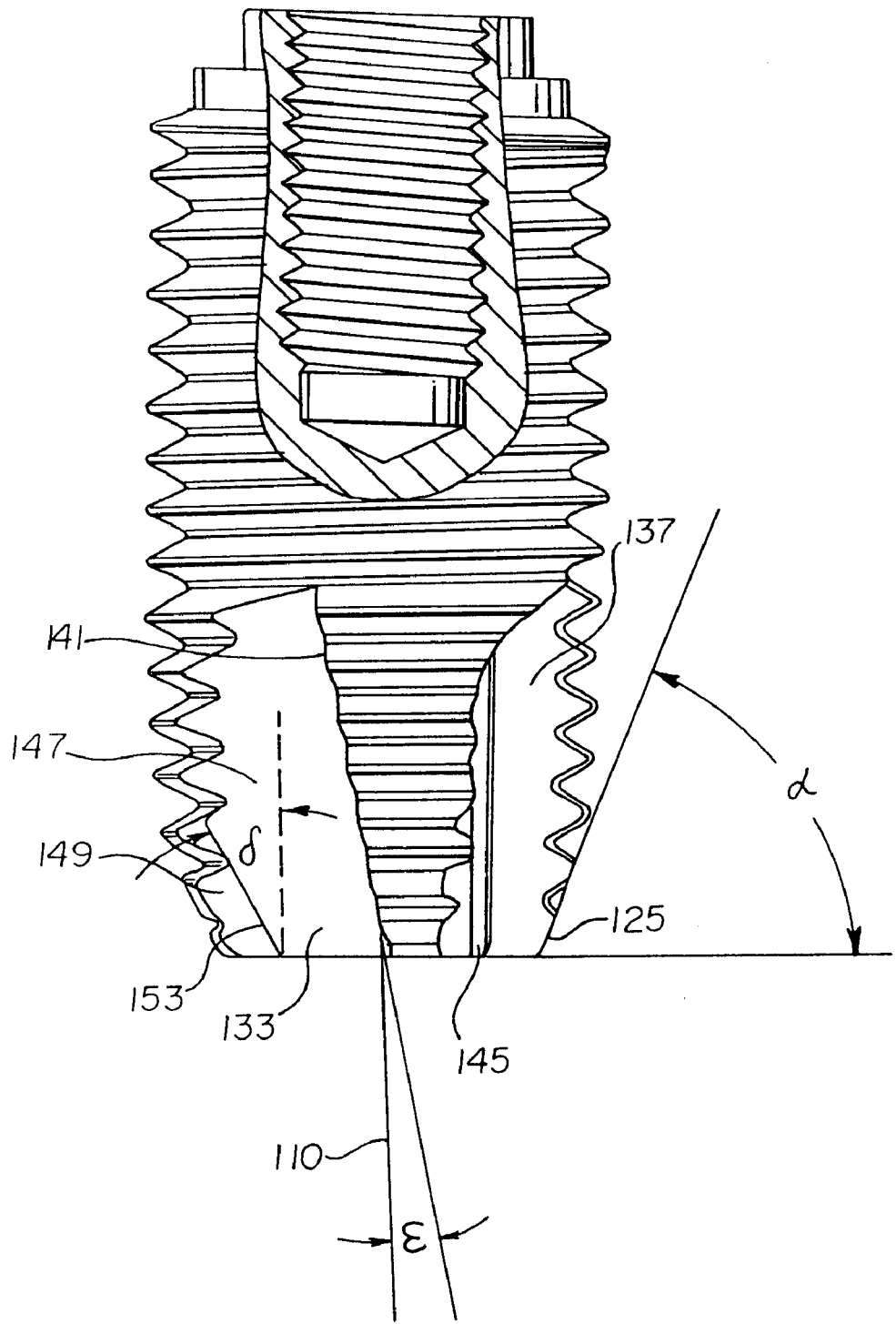
FIG. 8 is a perspective view of another embodiment of the invention.

In another embodiment of the invention, as shown in FIGS. 7 and 8, the relief surface may also be chamfered. Line 1 53 defined by the intersection of flat region 145 and relief surface 149 is at an acute angle, henceforth, referred to as the relief chamfer, denoted by δ, relative to the longitudinal axis 110 of the implant. Relief chamfer δ is desirably chosen such that line 153 tapers outward at a steeper angle than apical implant tip chamfer 125. The preferred relief chamfer is about 30°.

Along edge 141 of cutting face 137 are a plurality of first cutting teeth 181. First cutting teeth 181 include one or more beveled cutting teeth 183 whose thread 185 is beveled a short distance behind cutting face 137 and one or more non-beveled cutting teeth 187. The thread behind non-beveled cutting teeth 187 is full. Desirably, non-beveled cutting teeth 187 are located along the screw body at region 124 of maximum diameter.

Optionally, cutting teeth 183 may have a thread which is beveled immediately behind cutting face 137. The beveling may result in the complete removal of thread as long as profile of thread is present in cutting face 137.

Cavity 133 also has second non-cutting teeth 189 along the relief surface and surface 146. Non-cutting teeth 189 include one or more non-beveled teeth 191 and one or more beveled teeth 193.

In yet another embodiment of the invention, cutting faces 137 are angled from about 0° to about 25° relative to the longitudinal axis of the implant as depicted in FIG. 8. This angle, denoted by ε, is henceforth referred to as the forward flute angle. A desired embodiment has cutting faces 137 angled at a 10° forward angle. Forward angled cutting faces curl and chip the bone downwards into cavities 133. The bone tissue collected in cavities 133 promotes newly formed bone tissue to grow into cavities 133 and reduces the possibility of the implant unscrewing.

The length of chip cavities 133 along longitudinal axis 110 of implant 1 should be sufficient to allow for one or more full thread patterns along the cutting edge 141 of the cutting face 137.

In a preferred embodiment of the invention, the cutting flute will have a 10° forward flute angle, a 5° to 7° positive rake angle, a 70° apical implant chamfer, a 30° flat relief angle and a 35° relief chamfer angle. The implant will have four cutting faces and cavities equally spaced 90° apart. The length of the chip cavity provides at least three full thread forms on the cutting edge of the flutes.

The total volume of the cavities is sufficient to accommodate the bone tissue that has been scraped although in the embodiments shown in the figures, at least some of the bone material will escape out the bottom of the cavity and further into the bore hole.

In another embodiment, the invention is directed to a dental implant, such as the one shown generally at 100. Lower end 122 has at least one opening 133 therein and at least one threaded portion 211. Threaded portion 211 terminates in a plurality of first cutting teeth 181 at opening 133. Threaded portion 211 includes at least one beveled portion 213 which terminates in one or more cutting teeth 183 and at least one nonbeveled portion 215 which terminates in one or more cutting teeth 187.

Figure 9:
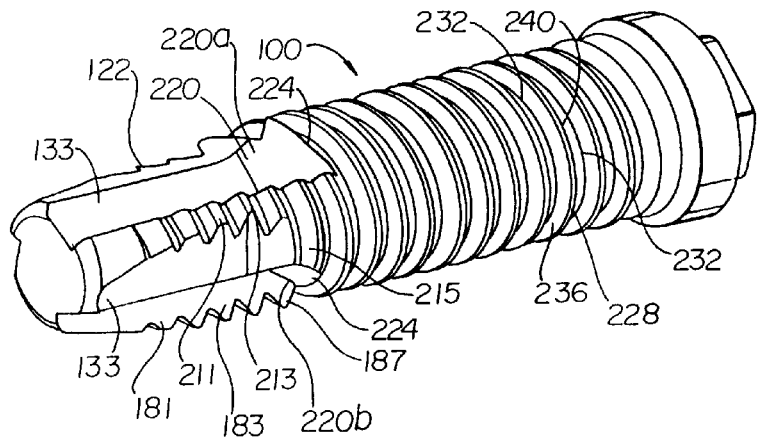
FIG. 9 is another perspective view of the implant shown in FIG. 1.

The invention is also directed to a dental implant having a plurality of circumferentially adjacent cavities with at least two of the cavities extending upward to a different height along the longitudinal axis of the implant. The cavities extend to different heights along the implant in order to blend the cavities into the thread. With reference to FIG. 9, circumferentially adjacent cavities 133 each have an uppermost surface 220 which blends into thread. The uppermost part 220a of at least one cavity is disposed further along the thread toward the top of the implant than the uppermost part 220b of at least one other cavity 220b. Desirably, all of the uppermost parts 220 of cavities 133 will be longitudinally displaced relative to each other along the cavity.

Figure 10A:
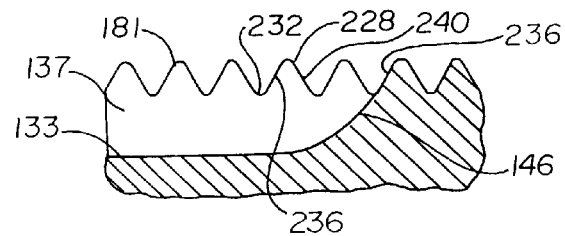
FIG. 10a an alternate fragmentary profile of the implant of FIG. 4 taken along line 10—10.
Figure 10B:
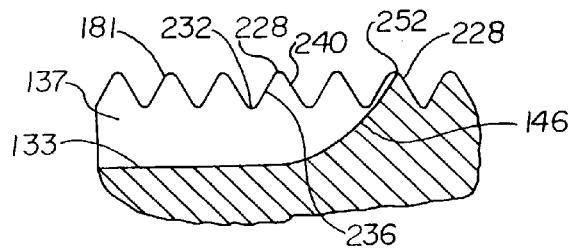
FIG. 10b an alternate fragmentary profile of the implant of FIG. 4 taken along line 10—10
Figure 10C:
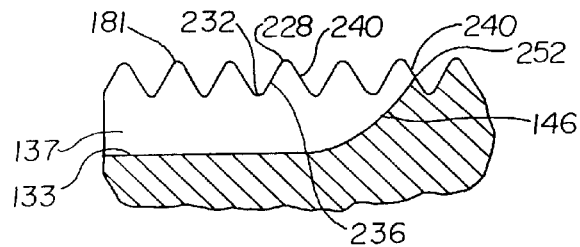
FIG. 10c an alternate fragmentary profile of the implant of FIG. 4 taken along line 10—10.

The invention also contemplates a self-tapping screw shaped dental implant where the upper portion of each cavity is bounded by an edge which lies along the thread and is substantially parallel to the thread. As shown in FIG. 9, each uppermost part of each cavity 220 terminates in an edge 224 substantially parallel to the thread. Having edges substantially parallel to the thread rather than cutting across the thread reduces jaggedness of the resulting cut and results in reduced drag and torque. The thread may be more fully characterized as having a crest surface 228 where the diameter of the thread is at a local maximum and a root surface 232 where the diameter of the thread is at a local minimum. Leading surface 236 extends from crest 228 surface downward toward root surface 232. Trailing surface 240 extends from crest surface 228 upward toward root surface 232. Desirably, each cavity 133 terminates in a leading surface 236 thereby avoiding the jagged edge that would result from terminating the cavity in a trailing surface or a crest surface. FIGS. 10a–10c illustrate the desired smooth transition that is achieved by terminating cavity 133 in a leading surface 236 as well as the jagged edge 252 that results from terminating cavity 133 in crest 228 or trailing surface 240.

The invention also contemplates cutting teeth which are beveled immediately behind cutting face.

Figure 11:
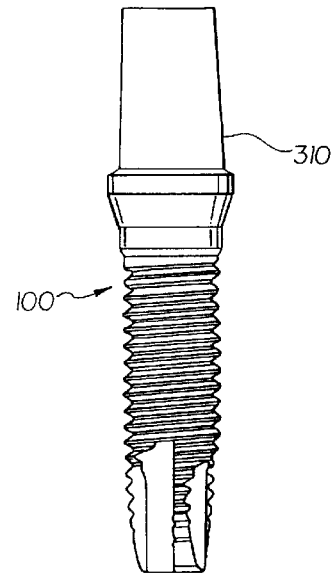
FIG. 11 is a side elevational assembly showing an inventive implant with an abutment mounted thereon.
Figure 12:
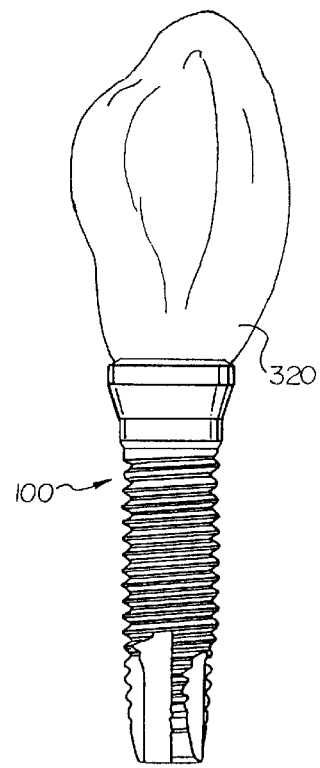
FIG. 12 is a side elevational assembly showing an inventive implant with a tooth mounted thereon.
Figure 13:
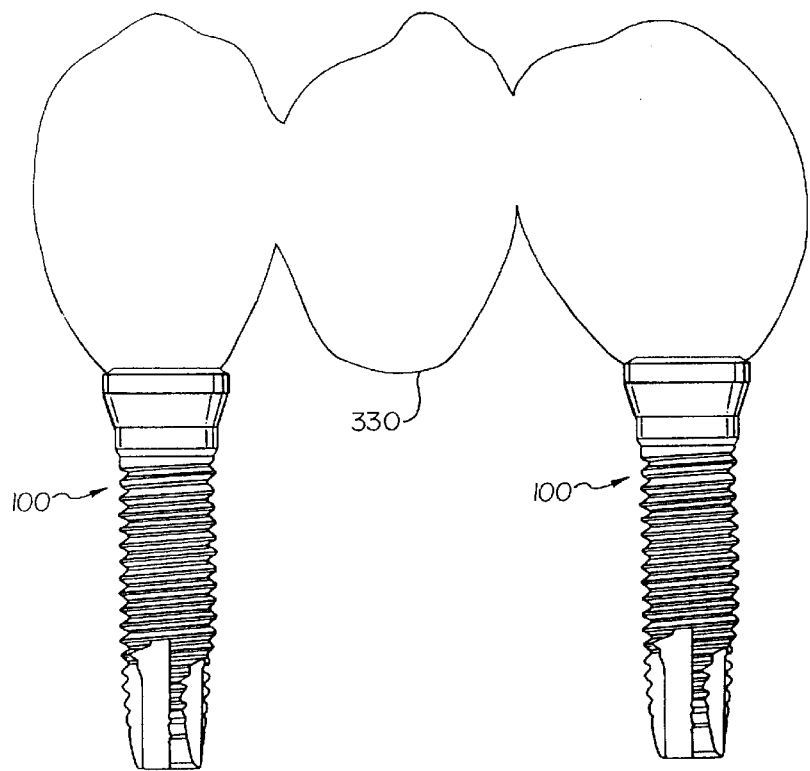
FIG. 13 is a side elevational assembly showing an inventive implant with a bridge mounted thereon.

The present invention is also directed to the inventive dental implant 100 described above in combination with an abutment 310 mounted thereon, as shown in FIG. 11, an artificial tooth 320 mounted thereon, as shown in FIG. 12, a tooth bridge 330 mounted thereon, as shown in FIG. 13, or any other suitable prosthesis mounted thereon.

The inventive implant may be coated with a material to facilitate healing and/or bone growth or treated in a manner to increase the surface area of the implant. For instance, the outer surfaces of the implant may be coated with hydroxyapatite, thereby providing a matrix for bone growth. Preferably, the coating will extend over the length of the external thread of the implant. As the wound heals, the hydroxyapatite may be resorbed into the bone. In another embodiment, a titanium plasma spray (TPS) is applied to the outer surfaces of the implant, again, preferably over the length of the external thread of the implant. In yet another embodiment, the implant is treated with resorbable blast media (RBM) comprising titanium beads and hydroxyapatite. Preferably, the RBM treatment extends from the base to approximately ⅔ of the length of the implant. All of these treatments can be obtained from Bio-coat, Southfield, Mich. All of these treatments are preferably applied as a final step following formation of the cutting flute. In the latter two cases, the treatment roughens the surface of the implant, thereby increasing the surface area of the implant. Where hydroxyapatite is used, one must take into account the dimension of the coating. Of course, other suitable coatings and treatments may be used as well.

The above disclosure are intended to be illustrative and not exhaustive. This example and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A self-tapping screw-shaped dental implant having an upper portion and a lower portion and formed of a screw body with an external thread, the lower portion having at least one longitudinal cavity formed therein, the cavity forming a cutting face with a cutting edge to provide self-tapping, the cutting edge having a plurality of cutting teeth including
at least one cutting tooth provided with a beveled relief surface defined on the outer surface of the implant behind the cutting tooth and
at least one cutting tooth with a full threaded outer surface of the implant behind the cutting tooth.

2. The implant of claim 1 wherein the lower portion includes a tip portion at the bottom, the tip tapering inward at an angle of from about 0° to about 2° relative to the longitudinal axis of the implant.

3. The implant of claim 1 wherein the lower portion is frustoconical.

4. The implant of claim 1 wherein the upper portion is frustoconical.

5. The implant of claim 1 having a plurality of longitudinal cavities formed therein.

6. The implant of claim 1 having three longitudinal cavities formed therein.

7. The implant of claim 6 wherein the cavities are symmetrically distributed about the screw body of the implant.

8. The implant of claim 1 further comprising a non-threaded collar section extending upward from the upper portion.

9. The implant of claim 8 wherein the collar section has a smooth surface.

10. The dental implant of claim 1, wherein the implant is made of commercially pure titanium.

11. The dental implant of claim 1 in combination with a restorative object selected from the group consisting of abutments, artificial teeth, and bridges.

12. The dental implant of claim 1 wherein the screw body has an outer surface, and the outer surface has been treated with a treatment selected from the group consisting of hydroxyapatite coating, titanium spray coating and resorbable blast medium processing so as to roughen the outer surface.

13. The dental implant of claim 1 wherein the screw body is tapered inward from a region of maximum diameter along the screw body.

14. The dental implant of claim 13 wherein the screw body tapers inward toward the bottom of the implant.

15. The dental implant of claim 14 wherein the screw body tapers inward toward the top of the implant.

16. The dental implant of claim 1 wherein the at least one cavity has a plurality of beveled cutting teeth.

17. The implant of claim 1 wherein the lower portion terminates in a base and the at least one longitudinal cavity terminates at the base.

18. A self tapping screw-shaped dental implant having a screw body with an external thread, the body having a longitudinal axis, a top, an upper portion with an attachment means for attaching a dental prosthesis thereto, a base lying in a plane perpendicular to the longitudinal axis, a lower portion having at least one chip cavity therein, the cavity defined by at least two surfaces including:
   a) a cutting face surface having a cutting edge with first cutting teeth;
   b) a second surface disposed at an angle relative to the cutting face surface, the second surface including at least a plurality of second teeth including at least one beveled tooth and at least one tooth which is not beveled.

19. The implant of claim 18 having an apical implant chamfer of about 50° to about 90° relative to the base.

20. The implant of claim 18 wherein the cutting face is oriented at a forward flute angle of about 0° to about 10° relative to the longitudinal axis of the implant.

21. The implant of claim 15 wherein the second surface includes a flat region and a concave region, the intersection between the cutting face and the flat region of the the second surface defining a corner line, the cutting face disposed at a rake angle, relative to a radial plane intersecting the corner line, the rake angle ranging from about 1° to about 25°.

22. The implant of claim 19 wherein the at least one beveled tooth forms a relief surface, the relief surface disposed at a flat relief angle with the flat region, wherein the flat relief angle is from about 20° to about 40°.

23. The implant of claim 22 wherein the intersection of the relief surface and the flat region define a line which is at a relief chamfer angle relative to the longitudinal axis of the implant, the relief chamfer angle tapering outward at a steeper angle than the apical implant tip chamfer.

24. The dental implant of claim 18 wherein the at least one tooth which is not beveled is closer to the top of the implant than the at least one beveled tooth.

25. The implant of claim 18 wherein the at least one cavity terminates at the base.

26. A dental implant consisting of a threaded body including an upper portion and a lower portion, the lower portion of substantially frustoconical shape, the lower portion having at least one opening therein and at least one threaded portion, the threaded portion terminating in a plurality of cutting teeth at the opening, the threaded portion including at least one beveled portion which terminates in a cutting tooth and at least one non-beveled portion which terminates in a cutting tooth.

27. The dental implant of claim 26 having a plurality of openings therein and a plurality of threaded portions extending between the openings wherein each threaded portion terminates in a plurality of cutting teeth at an opening, each threaded portion including at least one beveled portion which terminates in a cutting tooth and at least one non-beveled portion which terminates in a cutting tooth.

28. The implant of claim 26 wherein the upper portion is substantially frustoconical shaped.

29. The dental implant of claim 26 comprising three or four cavities equally spaced about the periphery of the implant.

30. The implant of claim 26 wherein the lower portion terminates in a base and the at least one opening extends to the base.

31. A self-tapping screw shaped dental implant and a thread thereon, the implant having an upper portion terminating in a top and a lower portion terminating in a base, the lower portion having a plurality of circumferentially adjacent cavities therein, each cavity having an uppermost part, the uppermost part of at least one cavity disposed closer to the top than the uppermost part of at least one other cavity wherein each cavity has an upper surface, each upper surface terminating in a portion of the thread, wherein each upper surface is substantially parallel to the thread.

32. The implant of claim 31 wherein the lower portion of the implant includes a base and the cavities terminate at the base.

\* \* \* \* \*